United States Patent
Likhotvorik et al.

(10) Patent No.: US 6,946,556 B1
(45) Date of Patent: Sep. 20, 2005

(54) PREPARATION OF OPIOID ANALGESICS BY A ONE-POT PROCESS

(75) Inventors: Igor Likhotvorik, Culver, IN (US); Joseph J. Lisowski, Knox, IN (US)

(73) Assignee: Acura Pharmaceuticals, Inc., Palatine, IL (US)

( * ) Notice: Subject to any disclaimer, the term of this patent is extended or adjusted under 35 U.S.C. 154(b) by 0 days.

(21) Appl. No.: 10/851,528

(22) Filed: May 21, 2004

(51) Int. Cl.$^7$ ............................................. C07D 489/00

(52) U.S. Cl. .......................................... 546/45; 546/39

(58) Field of Search ................................. 546/45, 39

(56) References Cited

U.S. PATENT DOCUMENTS

| | | | |
|---|---|---|---|
| 2,544,291 A | | 3/1951 | Baiser |
| 2,649,454 A | | 8/1953 | Rapoport |
| 2,654,756 A | | 10/1953 | Homeyer |
| 5,366,979 A | * | 11/1994 | Lawson ....................... 514/282 |
| 5,571,685 A | | 11/1996 | Hailes et al. |
| 5,847,142 A | | 12/1998 | Mudryk et al. |
| 6,008,356 A | * | 12/1999 | Kim et al. ..................... 645/56 |
| 6,013,796 A | * | 1/2000 | Huang et al. ................. 544/125 |
| 6,235,906 B1 | * | 5/2001 | Sebastian ..................... 546/45 |
| 6,365,742 B1 | * | 4/2002 | Mudryk et al. ............... 546/44 |
| 6,403,798 B2 | * | 6/2002 | Chiu et al. .................... 546/45 |
| 6,469,170 B1 | * | 10/2002 | Chiu et al. .................... 546/45 |
| 6,512,117 B1 | * | 1/2003 | Harclerode et al. ........... 546/45 |

FOREIGN PATENT DOCUMENTS

| | | |
|---|---|---|
| DE | 441613 | 3/1927 |
| WO | WO 0134608 | 5/2001 |

OTHER PUBLICATIONS

Black, H.T. et al., Synthetic Communications, V. 30, No. 17, pp. 3195-3201, (2000), Copyright by Marcel Dekker, Inc.

Findlay, Stephen P. et al., Journal of the American Chemical Society, *"The Preparation and Properties of Codeinone,"* V. 72, pp. 3247-3249, Jul., 1950.

Mannich, C. et al., Arch. Pharm. *"Ueber zwei neue Reduktionsprodukte des Kodeins,"* V. 258, pp. 295-316, Selbatverlag des Deutschen Apotheker-Vereins, Berlin, (1920).

Rapoport, H. et al., The Journal of Organic Chemistry, *"The Preparation of Some Dihydro Ketones in the Morphine Series by Oppenauer Oxidation,"* V. 15, No. 4, pp. 1103-1107, Jul., 1950, Published by The Williams & Wilkins Company, Baltimore, MD, USA.

Wieland, Heinrich, et al., Annalen der Chemie., vol. 433, pp. 267-271, (1923), Verlag Chemie, GmbH., Leipzig u. Berlin, printed in Germany.

* cited by examiner

Primary Examiner—Amelia Averill Owens
(74) Attorney, Agent, or Firm—Morgan Lewis & Bockius, LLP

(57) ABSTRACT

A one-pot process for preparing opioid analgesics such as hydrocodone, hydromorphone, and analogues thereof by reacting codeine, morphine, and analogues thereof with hydrogen in a solvent system of benzophenone and neutral solvent in the presence of a metal catalyst followed by oxidation in the presence of potassium tert-alkylate.

27 Claims, No Drawings

PREPARATION OF OPIOID ANALGESICS BY A ONE-POT PROCESS

FIELD OF THE INVENTION

The present invention relates to a process for the preparation of opioid analgesics such as hydrocodone, hydromorphone, and analogues thereof by a one-pot process.

BACKGROUND OF THE INVENTION

Hydrocodone and hydromorphone are widely used semi-synthetic narcotic analgesics possessing also useful antitussive properties. Hydrocodone is also an important intermediate for the synthesis of other opioid analgesics, e.g. dihydrocodeine.

Hydrocodone has been prepared by reduction of codeinone (Arch. Pharm (1920), 258, 295; J. Am Chem. Soc (1950), 72, 3247, U.S. Pat. No. 5,571,685) or thebaine (DE Pat. No. 441,613). However, since codeinone is obtained by oxidation of codeine in low to moderate yields, and thebaine is a relatively scarce alkaloid, these methods have little practical value.

A number of methods describe convenient one-pot isomerization of codeine to hydrocodone and morphine to hydromorphone in the presence of noble metal catalysts (examples may be found in "The Chemistry of the Morphine Alkaloids" by Bentley, K. W.; U.S. Pat. No. 2,544,291; U.S. Pat. No. 5,847,142, WO Pat. No. 0134608). Unfortunately these processes require large amounts of expensive metals of the platinum group, or call for exotic organometallic catalysts. Also isomerization is complicated by uncontrollable side reactions, requiring introduction of laborious purification procedures, and resulting in substantial yield loss.

Hydrocodone and hydromorphone have been prepared by Oppenauer oxidation of dihydrocodeine or dihydromorphine correspondingly (U.S. Pat. No. 2,649,454; U.S. Pat. No. 2,654,756; Synth. Commun. (2000), 30, 3195). The starting materials for the oxidation, dihydrocodeine or dihydromorphine, may be synthesized by hydrogenation of morphine or codeine. Hydrogenation is typically performed in solvents, such as aqueous acetic acid (J. Org. Chem. (1950), 15, 1105), ethyl acetate (Synth. Commun. (2000), 30, 3195), or ethanol (Ann. (1923), 433, 269), that are not compatible with the reaction media for Oppenauer oxidation. This makes necessary solvent removal and isolation of the products of hydrogenation, and, compared to the convenient one-pot syntheses discussed above, adds additional steps to the process of hydrocodone or hydromorphone preparation.

A need thus remains for an efficient, economical, and practical process for the production of hydrocodone, hydromorphone and related compounds.

SUMMARY OF THE INVENTION

The present invention provides a one-pot process for the preparation of 4,5-epoxymorphinan compounds of formula (I)

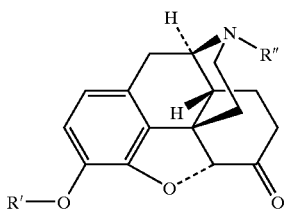

wherein
R' is hydrogen, methyl or alcohol protecting group;
R" is hydrogen, methyl or amine protecting group.
In one embodiment, the process includes the steps of
(i) reacting a compound of formula (II)

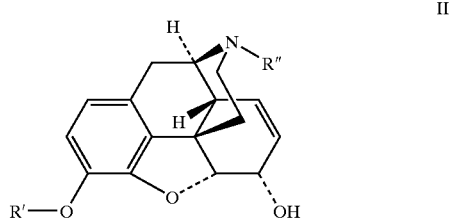

wherein R' and R" are as hereinbefore defined, with hydrogen in a solvent system of benzophenone and neutral solvent in the presence of a catalyst. In one embodiment, the catalyst is a metal catalyst. In one embodiment a metal catalyst is selected from VIII group of the Periodic Table of Elements. In one embodiment, the process generates a reaction mixture containing compound of formula (III)

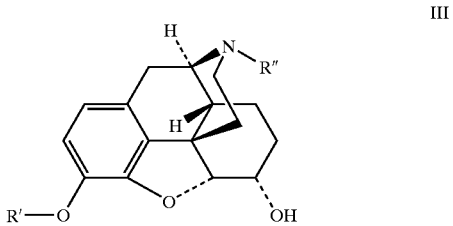

wherein R' and R" are as hereinbefore defined; and
(ii) reacting a compound of formula (III) with potassium tert-alkylate to yield a compound of formula (I).

DETAILED DESCRIPTION OF THE INVENTION

In one embodiment, the present invention provides a one-pot process for the preparation of 4,5-epoxymorphinan ketones of formula (I) with desirable purity and high yield from the corresponding allyl alcohols of formula (II). A reaction mixture containing saturated alcohol of formula (III) is generated by catalytical hydrogenation of allyl alcohol of formula (II) in a solvent system of benzophenone and neutral solvent (step i), and then reacted with potassium tert-alkylate, resulting in oxidation of the alcohol of formula (III) to a ketone of formula (I) as illustrated by Scheme 1 below:

Scheme 1

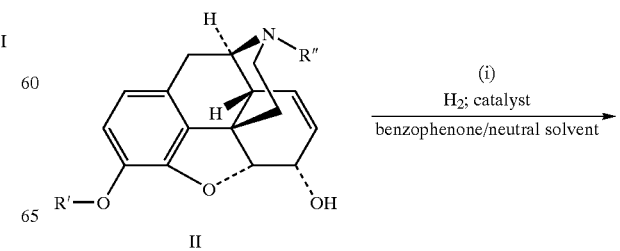

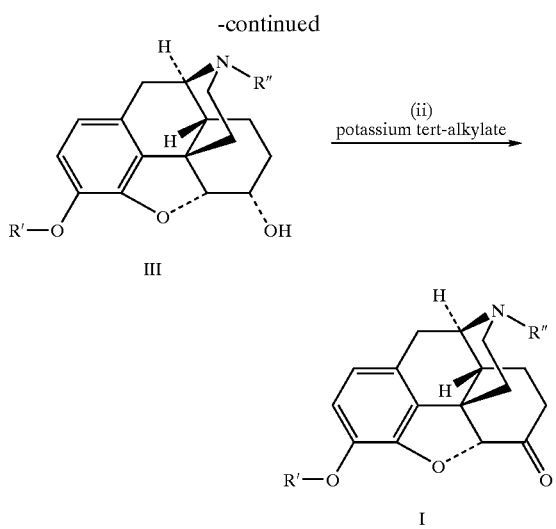

wherein

R' is hydrogen, methyl, or alcohol protecting group;
R" is hydrogen, methyl, or amine protecting group.

In one embodiment, a suitable alcohol protecting group may be an alkyl, aryl, benzyl or trisubstituted silyl group. Suitable amine protecting groups may be alkyl, aryl, benzyl, substituted alkoxycarbonyl, and substituted acetyl group. The protective groups and their use are described in much detail in "Protective Groups in Organic Synthesis" by T. W. Green and P. G. M. Wuts, Wiley-Interscience, New York, 1999. In one embodiment, suitable alcohol protecting groups can include, but are not limited to, one or more of methoxymethyl; methoxythiomethyl; benzyloxymethyl; p-methoxybenzyloxymethyl; p-anisyloxymethyl; t-butoxymethyl; 2-methoxyethoxymethyl; 2-(trimethylsilyl)ethoxymethyl; menthoxymethyl; tetrahydropyranyl; tetrahydrothiopyranyl; 1-ethoxyethyl; 1-[2-(trimethylsilyl)ethoxy]ethyl; 1-methyl-1-phenoxyethyl; 2-trimethylsilylethyl; t-butyl; p-chlorophenyl; p-methoxyphenyl; benzyl; 3,4-dimethoxybenzyl; 2,6-dichlorobenzyl; p-phenylbenzyl; 2,6-difluorobenzyl; 2-picolyl; 2-quinolinylmethyl; 1-pyrenylmethyl; diphenylmethyl; trimethysilyl; triethylsilyl; triisopropylsilyl; dimethylisopropylsilyl; diethylisopropylsilyl; dimethylthexylsilyl; t-butyldimethylsilyl; t-butyldiphenylsilyl; triphenylsilyl; and diphenylmethylsilyl groups. In another embodiment, suitable amine protecting groups can include, but are not limited to, one or more of t-butyl; [2-(trimethylsilyl)ethoxy] methyl; 2,4-dimethoxybenzyl; benzyl; 4-methoxybenzyl; diphenylmethyl; bis(4-methoxyphenyl)methyl; 5-dibenzosuberyl; triphenylmethyl; (4-methoxyphenyl)diphenylmethyl; 9-phenylfluorenyl; methoxycarbonyl; ethoxycarbonyl; cyclohexyloxycarbonyl; diisopropylmethoxycarbonyl; phenoxycarbonyl; 1-methylcyclohexyloxycarbonyl; (9-fluorenyl)methoxycarbonyl; 17-tetrabenzo[a,c,g,i]fluorenylmethoxycarbonyl; 2-(trimethylsilyl)ethoxycarbonyl; 2-phenylethoxycarbonyl; t-butoxycarbonyl; 1-adamantyloxycarbonyl; benzyloxycarbonyl; p-methoxybenzyloxycarbonyl; 3,5-dimethoxybenzyloxycarbonyl; acetyl; chloroacetyl; trichloroacetyl; trifluoroacetyl; phenylacetyl; phenylpropionyl; and benzoyl.

In one embodiment, the solvent system of benzophenone and neutral solvent provides desirable solubility of compounds of formula (III) throughout the process (steps i–ii), yet has sufficient compatibility with the reaction media for Oppenauer oxidation (step ii), particularly with alkylates, including potassium tert-alkylate and the reactive intermediates.

Suitable neutral solvents for use herein include, but are not limited to, solvents that are miscible with benzophenone, and are non-reactive within the limits of reactions conditions, such as hydrocarbons, for example, cyclohexane, toluene and heptane, ethers, for example, diisopropyl ether, tetrahydrofuran, 1,4-dioxane and methyl-tert-butyl ether, tertiary alcohols, such as tertbutyl alcohol and tert-amyl alcohol and combinations thereof.

In one embodiment, the molar ratio of compound of formula (II) to benzophenone can be in the range of about 1:3 to about 1:20, preferably of about 1:5 to about 1:12, most preferably of about 1:6 to about 1:9.

Furthermore, in one embodiment benzophenone concentration in the the solvent system should be sufficient to accomplish dissolution of the saturated alcohol of formula (III) produced in hydrogenation step (i). This is achieved by conveniently keeping benzophenone concentration from about 5% to about 99%, preferably from about 10% to about 75%, most preferably from about 25% to about 50%.

In certain embodiments, catalysts may be supported or unsupported metals for heterogeneous hydrogenation and/or organometallic compounds for homogeneous hydrogenation. Suitable metals for use herein selected from the group consisting of nickel, palladium, rhodium, ruthenium, and platinum.

In certain embodiments, the catalyst support for heterogeneous hydrogenation may be any inert substance, such as carbon, barium sulfate, silicon oxide, calcium carbonate, alumina and combinations thereof.

Catalysts for homogeneous hydrogenation should have sufficient solubility in the said solvent system. Numerous examples may be found in "Homogeneous Hydrogenation" by P. A. Chaloner, M. A. Esteruelas, F. Joo, L. A. Oro, Kluwer Academic Publishers, 1994. In one embodiment, a suitable catalyst for homogenous hydrogenation includes, but is not limited to, one or more of (bicyclo[2.2.1]hepta-2,5-diene)[1,4-bis(diphenylphosphino)butane]rhodium (I) Tetrafluoroborate; bis(bicyclo[2.2.1]hepta-2,5-diene)dichlorodirhodium; (1,5-cyclooctadiene)bis(methyldiphenylphosphine)iridium(I) hexafluorophosphate; dichlorotris(triphenylphosphine)ruthenium(II); bis(benzonitrile)dichloropalladium (II); and dichlorobis(triphenylphosphine)platinum (II). In one embodiment, a suitable organometallic catalysts for homogeneous hydrogenation includes, but is not limited to, chlorotris(triphenylphosphine)rhodium (I) (Wilkinson's catalyst).

In some embodiments, the amount of the catalyst for hydrogenation is not critical and should be sufficient to maintain a desirable rate of the hydrogenation. A suitable amount of the catalyst may be 0.01–10 mol % based on the amount of the allyl alcohol of formula (II) employed. Preferably this amount is 0.05–5 mol %, particularly 0.25–3 mol %.

The hydrogenation is typically effected at temperatures in the range of about 5° C. to about 110° C., preferably of about 15° C. to about 60° C., and most preferably of about 20° C. to about 45° C. The hydrogen pressure is preferably about 0.1 MPa to about 5 Mpa, most preferably about 0.1 MPa to about 0.5 Mpa.

Suitable tert-alkylates for use herein selected from the group consisting of potassium tert-amylate and potassium tert-butylate, and combinations thereof.

In one embodiment, the potassium tert-alkylate may be present in the reaction mixture in amounts between about 1 to about 5 equivalents relative to the amount of compound of formula (II), preferably between about 1.4 to about 4 equivalents.

In one embodiment, reaction with potassium tert-alkylate is suitably carried at temperatures in the range of about 15° C. to about 110° C., preferably of about 20° C. to about 80° C., and most preferably of about 25° C. to about 60° C.

In another embodiment, the allyl alcohol having formula (II) is selected from the group of morphine, wherein R' is hydrogen and R" is methyl, and codeine, wherein R' and R" are both methyl.

In some embodiments, compounds of the formula (I) that may be prepared according to a process of the invention include hydromorphone, wherein R' is hydrogen and R" is methyl, and hydrocodone, wherein R' and R" are both methyl.

In one embodiment, the process in accordance with the invention can be performed on an industrial scale by adding compound of formula (II), benzophenone, and the catalyst to the neutral solvent, agitating the mixture under hydrogen pressure at suitable temperature until hydrogenation is completed, then adding potassium tert-alkylate and agitating the mixture at suitable temperature until the transformation to the ketone of formula (I) accomplished. The progress of chemical reactions can be monitored by any conventional analytical technique, e.g. thin layer chromatography (TLC) or high performance liquid chromatography (HPLC).

A compound of formula (I) can be isolated from the reaction mixture in accordance with techniques that are well known to those skilled in the art.

Certain embodiments of the process of the invention has the advantage that the intermediate saturated alcohols of formula (III) do not require isolation and that the preparation of 4,5-epoxymorphinan ketones of formula (I) may be achieved in less steps and less time than in processes described in the prior art, without related losses of yield, delivering the products in desirable purity. Furthermore, the process of the invention has the advantage that 4,5-epoxymorphinan ketones of formula (I) may be obtained more conveniently, and at lower cost than when obtained through the processes described in the prior art.

In one embodiment, the mixture can be quenched by adding a volume of 0.5N to 2.0N acetic acid, typically a volume of about 1.5N acetic acid, to the mixture with mixing and cooling in an ice bath.

The following examples are given to illustrate the present invention. It should be understood, however, that the invention is not to be limited to the specific conditions or details described in these examples. Throughout the specification, any and all references to a publicly available document, including but not limited to a U.S. patent, are specifically incorporated by reference.

EXAMPLE 1

One pot hydrocodone synthesis using Wilkinson's catalyst for homogeneous hydrogenation and potassium tert-amylate in cyclohexane/benzophenone solution:

Benzophenone (6.22 g), cyclohexane (22 mL), dried codeine (1.38 g) and chlorotris(triphenylphosphine)rhodium (I) (Wilkinson's catalyst) (0.22 g) were charged into a glass hydrogenation bottle. The bottle was evacuated and filled with hydrogen. The mixture was magnetically agitated at ambient temperature (24–28° C.) while the hydrogen pressure was maintained at 5–15 psi until the pressure drop caused by the hydrogen consumption stopped. A solution of potassium tert-amylate in cyclohexane (12 mL, 15.4% w/w) was charged into the bottle with the reaction mixture in one portion, the mixture was magnetically agitated under nitrogen at ambient temperature for 4 hours and quenched by adding 1.5N acetic acid (13 mL) to the solution with mixing and cooling in an ice bath. Alternatively, in another embodiment the solution may be quenched by adding the solution to 1.5N acetic acid with mixing and cooling in an ice bath. The mixture was filtered, aqueous layer was separated and the organic layer was extracted with 1.5N acetic acid (2 mL). Combined aqueous layer (14.5 mL) according to the assay by HPLC contains 89.7 mg/mL hydrocodone (94% yield), purity 95 area %.

EXAMPLE 2

One pot hydrocodone synthesis using 5% palladium on carbon catalyst for heterogeneous hydrogenation and potassium tert-butylate in cyclohexane/benzophenone solution:

Codeine (11.71 g), benzophenone (48.32 g), 5% palladium on carbon wet (67% water) catalyst (0.37 g), and cyclohexane (57 mL) were charged into a stainless steel autoclave. The autoclave was evacuated and filled with hydrogen. The mixture was mechanically agitated at ambient temperature (25–29° C.) while the hydrogen pressure was maintained at 19–38 psi until the pressure drop caused by the hydrogen consumption stopped. Cyclohexane (120 mL) was charged into the autoclave followed by solid potassium tert-butylate (16.22 g), the mixture was mechanically agitated under nitrogen at ambient temperature for overnight, and then quenched with 1.5N acetic acid (150 mL) with mixing and cooling in the ice bath. The mixture was filtered, aqueous layer was separated and the organic layer was extracted with 1.5N acetic acid (5 mL). Combined aqueous layer was washed with isopropyl acetate (12 mL) and assayed by HPLC. Aqueous solution (176 mL) contains 58.4 mg/mL hydrocodone (90% yield), purity 96 area %.

EXAMPLE 3

One pot hydromorphone synthesis using Wilkinson's catalyst for homogeneous hydrogenation and potassium tert-butylate in tert-butanol/benzophenone solution:

Dried morphine (0.324 g), benzophenone (1.47 g), chlorotris(triphenylphosphine)rhodium (I) (Wilkinson's catalyst) (0.055 g), and tert-butanol (6 mL) were charged into a glass hydrogenation bottle. The bottle was evacuated and filled with hydrogen. The mixture was magnetically agitated at ambient temperature (24–29° C.) at 16 psi for 16 hours. Potassium tert-butylate (0.804 g) was charged into the bottle with the reaction mixture in one portion, the mixture was magnetically agitated until all solids dissolved, then heated under nitrogen at 60° C. for 4.5 hours. After aging for additional 66 hours at ambient temperature the mixture was quenched with 1.5N acetic acid (6 mL) with mixing and cooling in the water bath, diluted with methanol to 250 mL in volumetric flask and assayed by HPLC. Solution contains 1.12 mg/mL hydromorphone (86% yield), purity 94 area %.

While the invention has been described in detail and with reference to specific embodiments thereof, it will be apparent to one skilled in the art that various changes and modifications can be made therein without departing from the spirit and scope thereof. Thus, it is intended that the present invention covers the modifications and variations of this invention provided they come within the scope of the appended claims and their equivalents. Further, each and every reference disclosed herein is hereby incorporated by reference.

What is claimed is:

1. A process for the preparation a compound of formula (I)

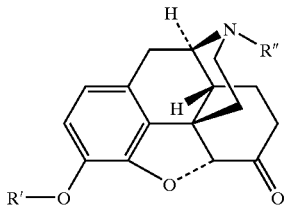

wherein R' is hydrogen, methyl or alcohol protecting group; R" is hydrogen, methyl or amine protecting group, comprising the steps of:

(i) reacting a compound of formula (II)

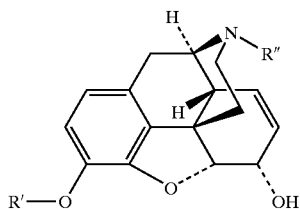

with hydrogen in a solvent system of benzophenone and neutral solvent in the presence of metal catalyst, to generate a reaction mixture containing compound of formula (III);

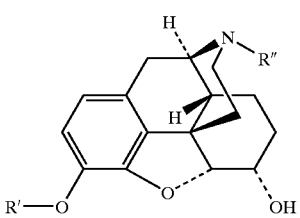

and (ii) reacting reaction mixture containing compound of formula (III) with potassium tert-alkylate to yield a compound of formula (I).

2. The process of claim 1, wherein the neutral solvent is selected from the group consisting of cyclohexane, toluene, heptane, diisopropyl ether, tetrahydrofuran, 1,4-dioxane, methyl-tert-butyl ether, tert-butyl alcohol, tert-amyl alcohol and combinations thereof.

3. The process of claim 1, wherein the metal catalyst is selected from the group consisting of nickel, palladium, rhodium, ruthenium, platinum, and combinations thereof.

4. The process of claim 1, wherein potassium tert-alkylate is selected from the group consisting of potassium tert-amylate and potassium tert-butylate, and combinations thereof.

5. The process of claim 1, wherein the molar ratio of compound of formula (II) to benzophenone is in the range of about 1:3 to about 1:20.

6. The process of claim 5, wherein the molar ratio of compound of formula (II) to benzophenone is in the range of about 1:5 to about 1:12.

7. The process of claim 6, wherein the molar ratio of compound of formula (II) to benzophenone is in the range of about 1:6 to about 1:9.

8. The process of claim 1, wherein the concentration of benzophenone in the said solvent system is in the range from about 5% to about 99%.

9. The process of claim 8, wherein the concentration of benzophenone in the said solvent system is in the range from about 10% to about 75%.

10. The process of claim 9, wherein the concentration of benzophenone in the said solvent system is in the range from about 25% to about 50%.

11. The process of claim 3, wherein metal catalyst is suitable for heterogeneous hydrogenation.

12. The process of claim 11, wherein the metal catalyst is supported on the support selected from the group consisting of carbon, barium sulfate, silicon oxide, calcium carbonate, alumina, and combinations thereof.

13. The process of claim 3, wherein the metal catalyst is suitable for homogeneous hydrogenation.

14. The process of claim 13, wherein the metal catalyst is chlorotris(triphenylphosphine)rhodium.

15. The process of claim 3, wherein the metal catalyst is present in the amounts from about 0.01 to about 10 mol % of the compound of formula (II).

16. The process of claim 15, wherein the metal catalyst is present in the amounts from about 0.05 to about 5 mol % of the compound of formula (II).

17. The process of claim 16, wherein the metal catalyst is present in the amounts from about 0.25 to about 3 mol % of the compound of formula (II).

18. The process of claim 1, wherein step (i) is performed at temperature range from about 5° C. to about 110° C.

19. The process of claim 18, which is performed at temperature range from about 15° C. to about 60° C.

20. The process of claim 19, which is performed at temperature range from about 20° C. to about 45° C.

21. The process of claim 1, wherein potassium tert-alkylate is present in amounts between about 1 to about 5 equivalents relative to the amount of compound of formula (II).

22. The process of claim 21, wherein potassium tert-alkylate is present in amounts between about 1.4 to about 4 equivalents relative to the amount of compound of formula (II).

23. The process of claim 1, wherein temperature in step (ii) is from about 15° C. to about 110° C.

24. The process of claim 23, wherein temperature is from about 20° C. to about 80° C.

25. The process of claim 24, wherein temperature is from about 25° C. to about 60° C.

26. The process of claim 1, wherein the compound of formula (I) is selected from the group consisting of hydrocodone, and hydromorphone.

27. The process of claim 1, wherein the metal catalyst is selected from group VIII of the Periodic Table of Elements.

* * * * *